United States Patent [19]

Wischniewski et al.

[11] 4,280,971
[45] Jul. 28, 1981

[54] PROCESS FOR THE PRODUCTION OF PANCREATIN PELLETS

[75] Inventors: Martin Wischniewski; Lutz Feicho, both of Neustadt; Gerhard Fischer; Guenter Peschke, both of Hanover, all of Fed. Rep. of Germany

[73] Assignee: Kali-Chemie Pharma GmbH, Hanover, Fed. Rep. of Germany

[21] Appl. No.: 89,963

[22] Filed: Oct. 31, 1979

[30] Foreign Application Priority Data

Jun. 8, 1979 [DE] Fed. Rep. of Germany ....... 2923279

[51] Int. Cl.³ .............................................. B22D 11/01
[52] U.S. Cl. ....................................... 264/15; 264/141
[58] Field of Search ................................. 264/15, 141

[56] References Cited
U.S. PATENT DOCUMENTS

| | | | |
|---|---|---|---|
| Re. 27,214 | 11/1971 | Nakahara | 264/15 |
| 3,154,603 | 10/1964 | Witheford et al. | 264/15 |
| 3,758,679 | 9/1973 | Seidler | 264/141 |

*Primary Examiner*—Donald E. Czaja
*Assistant Examiner*—James R. Hall
*Attorney, Agent, or Firm*—Schwartz, Jeffery, Schwaab, Mack, Blumenthal & Koch

[57] ABSTRACT

Pancreatin pellets are produced by a process employing extrusion techniques. In the process, a mixture of pancreatin powder and selected solvent is formed into a pliable mass suitable for extrusion. The extrusion is conducted followed by a cutting, shaping or forming of the extruded mass into pre-pellet like forms. Further drying and mechanical working of the pre-pellet forms results in the final pancreatin pellet of improved pharmaceutical and mechanical stability. A special aspect of the process is the selection of a solvent for mixing with pancreatin powder that is harmless to enzymes. Such solvents typically include isopropanol and acetone.

22 Claims, No Drawings

PROCESS FOR THE PRODUCTION OF PANCREATIN PELLETS

BACKGROUND OF THE INVENTION

The invention relates to a process for the production of pancreatin pellets, the pancreatin pellets produced by the process and medicines containing such pellets.

Pharmaceutical pellets are prepared mainly by two different techniques. In one technique utilizing suitable process apparatus (for example, pelletizing disks, fluidized beds or coating drums) a more or less spherical particle shape is built up from so-called seed grains by means of the alternating application of liquid and solid substances to the rolling or swirling seed grain. This is sometimes referred to as buildup granulation. In the other technique, the active ingredient is applied to the surface of prepared sugar globules.

Neither of these standard methods are particularly applicable to the production of pancreatin pellets. In buildup granulation, very large volumes of a liquid phase, consisting of water and/or various solvents are needed to build up the pellets. Water cannot be used in the production of pancreatin pellets because of the extreme sensitivity to humidity of the pancreas enzyme. Most of the other solvents utilized in building granulation are also more or less harmful to the enzyme. If a solvent that is harmless to the enzyme, such as isopropanol or acetone is applied, volumes which are multiples of the mass of the pellets are needed for their preparation; this is generally uneconomical and raises problems with respect to the emmission protection regulations. Frequently, pellets produced in this manner lack mechanical stability.

By the second method usually only relatively slight amounts of the active ingredient may be applied to the surface of the sugar globules exposed. This is possible only with the use of relatively large volumes of a liquid phase. Because, however, pancreatin preparations must be administered in single doses in considerable excess of 200 mg, this method is again not suitable for the preparation of pancreatin pellets.

SUMMARY OF THE INVENTION

It is, therefore, one of the objects of the invention to provide a process for the production of pancreatin pellets utilizing extruding techniques with a plastic mass comprising pancreatin powder and solvents harmless to enzymes. The process for producing pancreatic pellets comprises mixing together pancreatin powder and solvent harmless to enzymes, forming a pliable mass suitable for extrusion from the mixture of powder and solvent, extruding the pliable mass, shaping the extruded mass to pre-pellet or pellet-like forms, treating the forms by final mechanical working of the shaped forms into the desired final pancreatin pellet. An extruder press is employed possibly with cooling means. The extrusion is divided into cuttings, dried and processed further by conventional methods.

It has been found surprisingly that with the process of the present invention, pancreatin pellets with high pancreatin content and favorable mechanical properties may be produced under economical and environmentally satisfactory conditions.

In a specific embodiment of the process, pancreatin powder and a solvent harmless to enzymes are mixed into a plastic mass in a commercial mixer. A commercially available dry material is used as the pancreatin powder. Solvents harmless to enzymes are those which do not bring about a reduction in the activity of the enzymes contained in the pancreatin powder. The proportion of the pancreatin powder and the solvent is chosen so that the resulting mass may be extruded on an extruder press. For example, it is preferable to employ 70 ml to 200 ml per 1000 g pancreatin powder. Isopropanol and/or acetone represent preferred solvents harmless to enzymes. Pharmaceutically acceptable substances conventional in processes and products of this type, such as for example, binders and lubricants, may also be added.

Precautions must be taken during the extrusion so that the heat of compression generated will not damage the enzymes. For this purpose, in another preferred embodiment, the mixture to be extruded is precooled. The heat of compression may also be removed by means of additional cooling devices on the extruder itself. In another variant of the process, a low boiling component is added to the solvent and the extraction of energy which is effected by the evaporation of the low boiling component is utilized to cool the extraction or the cuttings, respectively. Particularly suitable additional components are chlorofluoro hydrocarbons which may be added in proportions of from 0 to about 50, and preferably, from about 15 to about 35% by volume of the total of the solvent used. All of these measures may be applied individually or in various combinations with each other.

In another embodiment of the present invention, the plastic mass is extruded through a perforated plate with a die bore or several such bores. Particularly preferred are die bores with circular cross sections. The diameter of the bores is not critical in principle and is, therefore, determined only by the subsequent pharmaceutical use of the pellets. Very good results have been achieved for example with diameters of about 0.5 to about 4 mm, preferably, about 1 to about 2.5 mm. On the one hand, pellets of this diameter are very readily processed and on the other, they are distributed very uniformly in the stomach in the chyme, resulting in a particularly high and uniformly efficient action.

After extruding the paste, cuttings are prepared by conventional methods. However, it has been found particularly advantageous to prepare cuttings having a ratio of diameter to length of 1:1. Such cuttings are readily processed.

For the subsequent processing, the cuttings are dried and further processed either directly or after rounding, into essentially spherical pellets.

In the rounding process, all of the known processes, such as, for example, deformation, tumbling and the like may be used. In a particular variant of the process, the pellets are rounded by the principle of buildup granulation by means of alternating surface wetting and coating with pancreatin powder.

Further processing of the raw or rounded pellets, may include all of the known further stages of processing. In particular, for example, coatings may be applied to the pellets. When coating the pellets, it is advisable to apply a coating resistant to stomach acid to protect the enzymes against the effects of the acid. It is thus advantageous under certain conditions to provide one or several coatings additionally, for example, to improve the adhesion, surface smoothing, etc.

The pellets produced by the process according to the invention may be finished directly as such, or for example, in the form of gelatin capsules. The process according to the invention is characterized by the following advantages:
(a) its operation is environmentally advantageous and economical;
(b) the diameter of the products may be varied within a wide range;
(c) the products of the process have pancreatin contents in excess of 80, preferably in excess of 85%, whereby high efficiencies of medications containing such pellets are obtained;
(d) the products of the process are distributed already in the stomach rapidly and uniformly in the chyme without disintegrating therein, in this manner optimum action of the pancreas enzyme may be obtained, particularly when, as provided for in an advantageous variant, the pellets are coated with a layer resistant to stomach acid, thus removing the pellets from the chemical attack of stomach acid.

The following examples merely explain the process of the invention and are not intended to further restrict the invention as claimed.

EXAMPLE 1

4400 g pancreatin are mixed in a laboratory mixer with 150 g magnesium stearate and wetted with approximately 400 ml isopropanol. The mixture is compressed in an extruder press with internal diameters of 1.6 mm and cut to strand lengths of 1.5–1.7 mm.

After drying, the cylindrical raw pellets are rounded in a coating drum to spherical pellets by the alternating application of a 1% isopropanol solution of polyvinylpyrrolidone (Kollidon K 25) and pancreatin. Approximately 1 liter of solution and 1800 g of pancreatin are needed.

The round pellets are smoothed by the application of a solution of 50 g polyethylene glycol 6000 in 100 ml isopropanol.

After drying, the pellets are coated to resist stomach acid in a GLATT fluidized bed apparatus (WSGD 5). To produce 6.3 kg pancreatin pellets, 7200 g of a solution of 590 g hydroxypropylcellulosephthalate (Type HP 44; manufactured by Shinetsu, Japan) and 150 g dibutylphthalate each in 3230 g methylene chloride and isopropanol are required.

The yield is approximately 7000 g of stomach acid resistant pellets each with a diameter of 1.6 to 2.0 mm and a content of approximately 86% pancreatin.

EXAMPLE 2

4400 l g pancreatin are wetted in a laboratory mixer with a mixture of 400 ml isopropanol and 200 g sym. tetrafluorodichloroethane (Kaltron$^R$ 114; manufactured by Kali-Chemi AG). The mixture is compressed in an extruder press with bores having internal diameters of 1.6 mm and cut to strand lengths of 1.5–1.7 mm.

After drying, the cylindrical raw pellets are rounded in a coating drum by means of the alternating application of a 1% solution of polyvinylpyrrolidone (Kollidon K 25) and pancreatin into spherically shaped pellets. For this purpose, approximately 1 liter solution and 1800 g pancreatin are needed. The round pellets are smoothed by applying a solution of 30 g Kollidon K 25 in 100 ml isopropanol.

After drying, the pellets are coated with a stomach acid resistant layer in a GLATT fluidized layer apparatus (WSGD 5). Herein for 6.1 g pancreatin pellets 7200 g of a solution of 590 g HP 55 and 150 g dibutylphthalate, each in 3230 g methylene chloride and isopropanol are required.

The yield consists of approximately 6800 g of stomach acid resistant pellets, each with a content of approximately 89% pancreatin.

What is claimed is:

1. A process for producing pancreatin pellets comprising mixing together pancreatin powder and a solvent harmless to pancreatin, forming a pliable mass suitable for extrusion from said mixture, extruding said pliable mass, pre-shaping the extruded mass into pre-pellet forms, drying said pre-pellet forms, and shaping said dried pre-pellet forms into pellets.
2. The process of claim 1 wherein said solvent is selected from the group consisting of isopropanol, acetone and mixtures thereof.
3. The process according to claim 2 wherein said solvent contains liquid chlorofluoro hydrocarbons.
4. The process of claim 1 wherein the extruded mass is cut into pre-pellet forms.
5. The process of claim 4 wherein said cut pre-pellets are formed into pellets by the generally uniform application of 1% solution of polyvinylpyrrolidone to said cut pre-pellets followed by the generally uniform application of pancreatin powder in repeating successive steps until spherically shaped pellets are formed.
6. The process of claim 4 wherein said pre-pellet forms are rounded into final pellets by tumbling said pre-pellet forms.
7. The process of claim 1 further comprising the step of coating said pellets with a pharmaceutically acceptable coating agent to render said pellet resistant to stomach acid.
8. The process of claim 1 further comprising a step of precooling said pliable mass prior to the extruding step.
9. The process of claim 3 wherein the amount of chlorofluoro hydrocarbon is up to about 50% by volume of the total amount of solvent.
10. The process of claim 3 wherein the amount of chlorofluoro hydrocarbon is from about 15 to about 35% by volume of the total amount of the solvents.
11. The process of claim 1 wherein the amount of solvent is from about 70 ml to about 200 ml per 1000 g of said pancreatin powder.
12. The process of claim 4 wherein the ratio of the diameter to the length of said cut forms is approximately 1:1.
13. The process of claim 1 further comprising the addition of pharmaceutically acceptable adjuvants in said mixing step.
14. The process of claim 13 wherein the final pellet contains more than about 80% by weight pancreatin.
15. The process of claim 13 wherein the final pellet contains more than about 85% by weight pancreatin.
16. The process of claim 5 wherein the final pellet contains more than about 80% by weight pancreatin.
17. The process of claim 5 wherein the final pellet contains more than about 85% by weight pancreatin.
18. The process oof claim 5 further comprising the addition of pharmaceutically acceptable adjuvants in the alternating coating step.
19. The pancreatin pellet formed by the process of claim 1.
20. The pancreatin pellet formed by the process of claim 16.
21. A pharmaceutical composition comprising a pancreatin pellet produced by the process of claim 1.
22. A pharmaceutical composition comprising a pancreatin pellet produced by the process of claim 16.

* * * * *